US006458869B1

(12) United States Patent
Antonucci et al.

(10) Patent No.: US 6,458,869 B1
(45) Date of Patent: Oct. 1, 2002

(54) ETCHANT/PRIMER COMPOSITION, ETCHANT/PRIMER/ADHESIVE MONOMER COMPOSITION, KITS AND METHODS USING THE SAME FOR IMPROVED BONDING TO DENTAL STRUCTURES

(75) Inventors: Joseph M. Antonucci, Kensington; Frederick C. Eichmiller, Ijamsville; Gary E. Schumacher, Gaithersburg, all of MD (US)

(73) Assignees: National Institute of Standards of Technology, Gaithersburg, MD (US); American Dental Association Health Foundation, Chicago, IL (US)

( * ) Notice: Subject to any disclaimer, the term of this patent is extended or adjusted under 35 U.S.C. 154(b) by 0 days.

(21) Appl. No.: 09/537,703

(22) Filed: Mar. 30, 2000

(51) Int. Cl.[7] .............................. A61K 7/24; A61K 7/16; C08F 20/26
(52) U.S. Cl. ...................... 523/118; 252/79.1; 252/79.2; 106/35; 424/55; 424/49; 427/307; 433/216
(58) Field of Search .............................. 216/33, 34, 83, 216/96; 523/118; 252/79.1, 79.2; 427/307; 424/55; 106/35; 433/216

(56) References Cited

U.S. PATENT DOCUMENTS

| 4,659,751 A | * | 4/1987 | Bowen ........................ 523/116 |
| 4,810,195 A | * | 3/1989 | Asussen et al. ............. 433/215 |
| 5,498,643 A | | 3/1996 | Antonucci et al. .......... 523/118 |
| 5,690,840 A | | 11/1997 | Antonucci et al. ............ 216/34 |
| 5,756,560 A | | 5/1998 | Antonucci et al. .......... 523/118 |

FOREIGN PATENT DOCUMENTS

EP 0284275 * 9/1988 ............ A61K/6/00

OTHER PUBLICATIONS

G.E. Schumacher et al., Abstract, "Acid–modified N–phenyliminodiacetic Acid as a Self–etching Primer for Dentin Bonding", 1997 IADR Abstract Form Orlando.

* cited by examiner

Primary Examiner—Randy Gulakowski
Assistant Examiner—Shamim Ahmed
(74) Attorney, Agent, or Firm—Banner & Witcoff, Ltd.

(57) ABSTRACT

The present invention is directed to an etchant/primer composition, an etchant/primer/adhesive monomer composition, kits using the same and methods using the same for improved bonding to dental structures. The etchant/primer composition comprises a compound having the formula:

$$RN(CH_2YCO_2M)_2$$

wherein $R=R^1$ or $R^2$;
$R^1$=an aromatic group;
$R^2$=a conjugated unsaturated aliphatic group;
Y=a single bond, $CH_2$, $CHCH_3$ or $C=CH_2$; and
each M is independently H, an alkali metal, an alkaline earth metal, aluminum, a transition or redox metal or an alkyl group having 1 to 18 carbon atoms, with the proviso that when both M groups are alkyl groups, said compound is capable of being easily hydrolyzed, displaced, or exchanged with other reagents present in the etchant/primer composition, a polar solvent system, and nitric acid. The etchant/primer/adhesive monomer composition comprises a compound having the formula (I) as noted above, a polar solvent system, an acid selected from the group consisting of nitric acid, hydrochloric acid, citric acid, lactic acid, glycolic acid, formic acid, pyruvic acid and combinations thereof, and adhesive monomer resin, and an initiator. The above-noted compositions are applied to dental structures requiring dental restoration for improved bonding of adhesive resins and polymers to dental structures.

26 Claims, No Drawings

ETCHANT/PRIMER COMPOSITION, ETCHANT/PRIMER/ADHESIVE MONOMER COMPOSITION, KITS AND METHODS USING THE SAME FOR IMPROVED BONDING TO DENTAL STRUCTURES

FIELD OF THE INVENTION

The present invention is directed to an etchant/primer composition, an etchant/primer/adhesive monomer composition, kits comprising the same and methods using the same for dental restorative applications. More particularly, the present invention is directed to an etchant/primer composition, an etchant/primer/adhesive monomer composition, kits comprising the same and methods using the same for improving the bond strength of adhesive resins bonded to dentin, enamel, bone, or other such dental structures.

BACKGROUND OF THE INVENTION

The restoration of decayed dental structures including caries, decayed dentin or decayed enamel, is often accomplished by the application of polymer based adhesives to the relevant dental structures. However, typically, polymer-based adhesive resins alone do not form strong bonds with dentin or enamel. To improve the adhesion of polymer-based resins to dentin or enamel, various pre-treatment steps are undertaken. Ordinary pre-treatment steps include an etching step followed by a priming step. Typically, after priming, the adhesive resin is applied as a polymeric adhesive resin or as polymer-forming monomer(s) polymerized on the dental structure in question.

During the etching step, an aqueous solution of inorganic or organic acids is applied to the relevant dental structure, e.g., dentin or enamel. The acid etches the enamel layer and removes the "smear layer" from dentin and demineralizes a surface layer of dentin. The "smear layer" is a coating of debris that forms on the dentin surface as a result of the cutting and grinding processes of, for example, cavity preparation. After etching, a "primer" is applied during the priming pre-treatment step. The "primer" improves the bonding between the subject dentin, enamel, or bone structure and the yet to be applied adhesive resin (or monomer(s) thereof).

The above-noted etchants, primers, resins and monomers are typically applied in a step-wise fashion. In addition to the step-wise etching, priming and polymerizing (applying and curing adhesive resins or monomers) steps, between these steps, one or more rinsing, drying, and rinsing/drying steps may be required. As a result, dental restoration involves using complex, technique-intensive, multi-step restorative procedures.

To simplify these complicated restorative procedures, it would be beneficial to provide a single composition that accomplishes at least both etching and priming. Thus, separate etching and priming steps desirably could be combined into a single step by applying a suitable combination etchant/primer composition. Additionally, it would be desirable to provide a single composition comprising an etchant, a primer, and an adhesive resin monomer. Finally, it would be desirable to provide a kit comprising the same and methods for using the same.

In an effort to formulate multi-component compositions, it was undertaken to investigate whether the addition of an acid to a primer such as N-phenyliminodiacetic acid (PIDAA) might improve the shear bond strength (SBS) of an adhesive resin such as PMDM (the reaction product of 2-hydroxyethyl methacrylate (HEMA) and pyromellitic acid dianhydride) or PMDGM (reaction product of glyceroldimethacrylate and pyromellitic acid dianhydride) bonded to dentin. A study was conducted to determine the effect on adhesive resin-dentin SBS by incorporating various acidic additives into a primer such as PIDAA.

In particular, various acids (10% w/w $H_3PO_4$, 5% w/w ascorbic acid (AA), or 2.8% w/w CPIDAA) added to 0.3M PIDAA (dissolved in acetone:$H_2O$ (1:1 v/v) solution) were evaluated for their effect on SBS. Additionally, a 0.6M PIDAA (dissolved in acetone:$H_2O$ (1:1 v/v)) solution was evaluated as a control for its effect on SBS. The bonding protocol utilized a two-step procedure: the first step was to apply a test self-etching primer (e.g., PIDAA with 10% w/w $H_3PO_4$, 5% w/w ascorbic acid or 2.8% w/w CPIDAA, respectively) to a dentin surface for 60 seconds which was then dried with a stream of air. The $H_3PO_4$ acid and ascorbic acid containing test specimens were rinsed with water and air dried. Thereafter, a 20% w/w adhesive resin of PMGDM (in acetone activated with 0.07% w/w camphorquinone (CQ; visible light photoinitiator)) was applied and light cured (LC) for 20 seconds. The light activated resin composite was then applied to the dentin previously treated with the acid modified or experimental self-etching primers and cured for 60 seconds. After 24 hours storage in $H_2O$ at 23° C., SBS values were measured. SBS values were measured in MPa units (SD, n=10). The results were as follows (MPa (SD)): $H_3PO_4$, 5.5 (7.9); AA, 9.1 (6.3); CPIDAA, 13.9 (6.2); and PIDAA (control), 16.9 (5.6). ANOVA indicated significant differences existed between the SBS values measured. Dunnett's multiple comparison test (p<0.05) showed that the SBS values compared as follows: $H_3PO_4 \approx AA < CPIDAA \approx PIDAA$.

These results indicated that adding an acid to an iminodiacetic acid primer such as PIDAA weakened the shear bond strength of the adhesive resin-dentin bond. See "1997 IADR ABSTRACT FOR—ORLANDO" submitted by G. E. Shumacher and J. M. Antonucci entitled "Etchant-Modified N-phenyliminodiacetic Acid as a Self-etching Primer for Dentin Bonding" (submitted September 20, 1996).

Accordingly, one of ordinary skill in the art would have been led to believe that the addition of an acid to an iminodiacetic acid primer yields a self-etching primer that weakens (rather than strengthens) the shear bond strength of an adhesive resin bonded to dental structures such as dentin. Thus, one of ordinary skill would not have been motivated to combine acid etchants with iminodiacetic acid primers to yield a single etchant/primer composition. Consequently, until now, the need for a single self-etching primer composition (e.g., etchant/primer composition or an etchant/primer/adhesive monomer composition) remained unfulfilled.

Accordingly, there is a need in the art for a single self-etching primer composition which does not weaken the SBS between an adhesive resin and the underlying dental structure being restored.

SUMMARY OF THE INVENTION

Thus, it is an object of the present invention to provide a single composition which is a self-etching primer composition (e.g., an etchant/primer composition or an etchant/primer/adhesive monomer composition) for dental restorative purposes that does not sacrifice the SBS between the subject dental structure and the adhesive resin bonded thereto. It is a further object of the present invention to provide a kit and a method for using the same.

These and other objects are accomplished by the embodiments described below. One embodiment of the present invention comprises an etchant/primer composition comprising:

a compound having the formula:

wherein R=$R^1$ or $R^2$;
$R^1$=an aromatic group;
$R^2$=a conjugated unsaturated aliphatic group;
Y=a single bond, $CH_2$, $CHCH_3$ or $C=CH_2$; and
each M is independently H, an alkali metal, an alkaline earth metal, aluminum, a transition or redox metal or an alkyl group having 1 to 18 carbon atoms, with the proviso that when both M groups are alkyl groups, the compound is capable of being easily hydrolyzed, displaced, or exchanged with other reagents present in the etchant/primer composition;
a polar solvent system; and
nitric acid.

According to another embodiment, a method of preparing a dental substrate for contact with an adhesive resin or an adhesive resin monomer is provided. This method comprises the step of contacting the substrate with an etchant/primer composition that comprises:

a compound having the formula:

wherein R=$R^1$ or $R^2$;
$R^1$ an aromatic group;
$R^2$=a conjugated unsaturated aliphatic group;
Y=a single bond, $CH_2$, $CHCH_3$ or $C=CH_2$; and
each M is independently H, an alkali metal, an alkaline earth metal, aluminum, a transition or redox metal or an alkyl group having 1 to 18 carbon atoms, with the proviso that when both M groups are alkyl groups, the compound is capable of being easily hydrolyzed, displaced, or exchanged with other reagents present in the etchant/primer composition;
a polar solvent system; and
nitric acid.

Other embodiments of the claimed invention are described below.

DETAILED DESCRIPTION OF THE INVENTION

Broadly, the etchant/primer composition in accordance with the present invention comprises an aryl- or alkenyl-iminodiacetic acid (or derivative thereof), a polar solvent system and nitric acid. Further, in general, the etchant/primer/adhesive monomer composition in accordance with the present invention comprises such iminodiacetic acids (or derivatives thereof), a polar solvent system, an acid, and an adhesive monomer.

The Iminodiacetic Acid

According to one embodiment, the etchant/primer composition of the present invention comprises a compound of formula (I):

 (I), a polar solvent system and nitric acid. The compound of formula (I) is an iminodiacetic acid or a derivative thereof (the term "iminodiacetic acid" as used herein is intended to mean the acid itself or its derivatives) wherein R=$R^1$ or $R^2$; $R^1$=an aromatic group; $R^2$=a conjugated unsaturated aliphatic group; Y=a single bond, $CH_2$, $CHCH_3$ or $C=CH_2$; and each M is independently H, an alkali metal, an alkaline earth metal, aluminum, a transition or redox metal or an alkyl group having 1 to 18 carbon atoms, with the proviso that when both M groups are alkyl groups, said compound is capable of being easily hydrolyzed, displaced, or exchanged with other reagents present in the etchant/primer composition. An example of an easily hydrolyzed group is t-butyl.

$R^1$ may be a heterocyclic aromatic group. Preferably, $R^1$ is a carbocyclic aromatic group, particularly a phenyl or napthyl group or derivatives thereof. Most preferred $R^1$ groups are substituted and unsubstituted phenyl groups. When substituted, the substituents may be electron donating or electron withdrawing and located at either the ortho, meta or para positions of the phenyl ring. However, when the substituent is of a sufficient size to impart steric hindrance, it is preferred that the substituent be located at the meta or para position. Preferred substituents are groups which are the same or similar to the iminodiacetic acid group or derivatives thereof which extend the conjugated system of the aromatic ring.

In the present invention, $R^1$ is preferably $C_6H_5$ or $C_6H_4R^3$, wherein $R^3=N(CH_2CO_2M)_2$; $C_6H_4N(CH_2CO_2M)_2$; $R^4O(CH_2)_2OC_6H_4N(CH_2CO_2M)_2$; $CH=CH_2$; $CO_2H$; F; Cl; Br; I; OH; SH; (m- or p-) $CH_2C_6H_4$(m- or p-) $CH=CH_2$; $OCOC(R^4)=CH_2$; $NR^4COC(R^4)=CH_2$; $(CH_2)_2OCOC(R^4)=CH_2$; $C_6H_5$; an alkyl group having 1 to 12 carbon atoms; $HOCH_2$; $HOCH_2CH_2$; $R^5_2N$; $R^6O$; $R^6S$; $R^6CO$; $R^7CONH$; $R^7COCO$, wherein $R^4$=H or $CH_3$; wherein each $R^5$ is independently H or an alkyl group having 1 to 8 carbon atoms and is preferably $CH_3$, or $C_2H_5$; wherein $R^6$=an alkyl group having from 1 to 6 carbon atoms, preferably $CH_3$; and wherein $R^7$=an alkyl group having 1 to 6 carbon atoms, preferably $CH_3$ or $CH_2CH_3$. Suitable for use as $R^1$ are also various derivatives of p-2-hydroxyethylphenyliminodiacetic acid or soluble salts thereof, such as $R^8$(p-$NHCOO(CH_2)_2C_6H_4N)CH_2CO_2M)_2)_2$ wherein $R^8$ is an alkyl group.

In the present invention, $R^2$ may be an unsaturated cycloaliphatic group, or more preferably, a linear or branched unsaturated aliphatic group, such exemplary aliphatic groups include carbon-to-carbon bonds, carbon-to-nitrogen bonds, or combinations thereof, which are conjugated, unsaturated bond(s). Within the aliphatic group may be other atoms such as N or O which are part of ester, carbonyl, ether, amino, imino, or amide groups or combinations thereof. The number of carbon atoms present within $R^2$ ranges from 4 to 20.

Preferably, $R^2$ includes one or more vinyl groups. Most preferably, $R^2$ includes a residue of crotonate ($CH_3CH=CHCO_2M$) or substituted crotonate groups present as the free acid, ester or salt of the type described herein for iminodiacetic acid salts. Preferred crotonate derivatives are those in which bonding to the nitrogen atom of the iminodiacetic acid group takes place either through the carbon atom number 2 or carbon atom number 3 of the crotonate residue, with the latter being the most preferred. In such an instance, $R^2$ represents $CH_3C=CHCO_2R^9$. $R^9$ represents M, wherein M has the same meaning as indicated above, including a vinyl group or an alkyl group having from 1 to 24 carbon atoms, preferably $CH_3$ or $CH_2CH_3$. Other preferred $R^2$ groups include the residue of cinnamic acid, present as the free acid, ester or its salt.

Iminodiacetic acids suitable for use in conjunction with the present invention include, but are not limited to, m- or p-vinyl-N-phenyliminodiacetic acid; N-p-acrylphenyliminodiacetic acid; methacrylamidophenyliminodiacetic acid; N,N-(carboxymethyl-2-carboxyallyl) aniline; N,N-bis(2-carboxyallyl)aniline; m- or p-vinyl, m- or p-benzyl-N-phenyliminodiacetic acid; N,N,N'N'-p-phenylenediaminotetraacetic acid; N,N'-(1,2-ethanediyl bis (oxy-2,1-phenylene)-bis-N-carboxymethyl) (also known as 1,2-bis(o-aminophenoxy-)ethane-N,N,N',N'-tetraacetic acid or BAPTA); o-, m-, or p-biphenylenediiminodiacetic acid; carboxy-N-phenyliminodiacetic acid; N-phenyliminodiacetic acid; and combinations thereof. The most preferred iminodiacetic acid is PIDAA, salts and esters thereof. Suitable examples of PIDAA salts include the dipotassium and magnesium salts thereof.

Many of the compounds of formula (I) used in the etchant/primer composition or the etchant/primer/adhesive monomer composition of the present invention are available from commercial sources. Where commercially unavailable, the synthesis of appropriate compounds in which $R^1$ is an aromatic group, such as a phenyl or a substituted phenyl group, may be achieved by the procedure described in Lin et al., *Synthesis*, 7, pp. 548–49 (July 1998). This method involves reacting the appropriate substituted or unsubstituted aniline with sodium chloroacetate in the presence of n-butyllithium as a base. Many of the compounds according to formula (I) in which $R=R^2$ may be prepared in a similar manner. Many of the olefinic compounds in which $R=R^2$ may be prepared by a method similar to that used to prepare the crotonyl-N-iminodiacetic acid compounds. For example, 3-aminocrotonic acid and its esters can be reacted with haloacetic acid or derivatives thereof, such as chloroacetic acid, to synthesize the analogous N,N-diacetic acid derivatives of crotonic acid, its esters, salts and the like using a mild base in an appropriate solvent. Alternatively, the aromatic or appropriate aliphatic amine may be reacted with haloacetic acid or a derivative thereof. In addition, iminodiacetic acid may be reacted with the appropriate conjugated unsaturated organic halide in an appropriate solvent and in the presence of a base such as triethylamine.

Polar Solvent System

Polar solvent systems suitable for use in conjunction with the present invention comprise water and/or a polar solvent which is partially or totally soluble in water. For dental applications, a suitable solvent system is one which completely wets and diffuses into the surface of the enamel and particularly dentin in a clinically acceptable period of time (on the order of about 15 to about 180 seconds). With reference to wetting and diffusing of the solvent system into enamel or dentin, such wetting and diffusing is preferably to a depth of not more than about 5 microns.

Examples of polar solvents suitable for use in conjunction with the present invention include, but are not limited to, low molecular weight ketones such as acetone and methyl ethyl ketone, low molecular weight alcohols such as propanol or ethanol, polar aprotic solvents such as dimethylformamide, dimethylacetamide, dimethylsulfoxide, 1-methyl-2-pyrrolidinone or combinations and mixtures thereof. Water or a mixed solvent system of water and acetone is preferred. In such a solvent system, the amount, by volume, of acetone may range from about 5% to about 90% acetone with the remainder being water. Preferred is a 1:1 by volume mixture of acetone and water. Water may be used more frequently as a component of the solvent system when the etchant/primer composition includes a water-soluble salt. Small amounts (e.g., about 1% by weight or slightly greater than 1% by weight) of surfactants may be used to enhance the solvent potential of these solvent systems.

The concentration of the iminodiacetic acid within the etchant/primer composition or the etchant/primer/adhesive monomer composition of the present invention may be varied. For example, when the iminodiacetic acid comprises PIDAA and the polar solvent system comprises acetone and water, the concentration of the iminodiacetic acid ranges from about 1% to about 20% by weight, based on a total weight of the etchant/primer composition or the etchant/primer/adhesive monomer composition being applied.

The Acid

The Etchant/Primer Composition

The acid selected should be sufficient to etch the dentin, enamel or other dental structure to facilitate improved adhesion of the adhesive resin or monomer thereto. In addition, the acid should be sufficient to permit the adhesive resin or monomer to wet, infiltrate or penetrate, and to conform to the vital dentinal or enamel substrate. The acid should also be sufficient to strengthen the SBS of the bond between the adhesive resin and the underlying dental structure. Such an acid for use in conjunction with the etchant/primer composition of the present invention is nitric acid.

In addition to the iminodiacetic acid and polar solvent system, the etchant/primer composition further comprises nitric acid provided in an amount, preferably, ranging from about 0.05% to about 5.0% by weight, based on a total weight of the etchant/primer composition. More preferably, the nitric acid is provided in an amount ranging from about 0.1% to about 2.5% by weight, based on a total weight of the etchant/primer composition.

The etchant/primer composition of the present invention is applied to the relevant dental structure for a time sufficient to pre-treat the dental structure prior to application of an adhesive resin, an adhesive resin monomer (containing an initiator e.g., a photo-initiator, a free-radical initiator, or other types of chemical initiator) or combinations thereof. Typically, time periods for applying the etchant/primer composition to the relevant dental structure range from about 15 seconds to about 180 seconds, preferably, from about 30 seconds to about 120 seconds, and most preferably, from about 30 seconds to about 60 seconds.

Etchant/Primer/Adhesive Monomer Composition

The acid selected should be sufficient to etch the dentin, enamel or other dental structure to facilitate improved adhesion of the adhesive resin or monomer thereto. In addition, the acid should be sufficient to permit the adhesive resin or monomer to wet, infiltrate or penetrate, and to conform to the vital dentinal or enamel substrate. The acid should also be sufficient to strengthen the SBS of the bond between the adhesive resin and the underlying dental structure.

Suitable acids for use with the etchant/primer/adhesive monomer composition of the present invention, include, but are not limited to, nitric acid, hydrochloric acid, lactic acid, glycolic acid, formic acid, pyruvic acid, citric acid, and strong acids that form chelating agents or combinations and mixtures thereof.

The acid is typically provided in an amount ranging from about 0.05% to about 5.0% by weight, based on a total weight of the etchant/primer/adhesive monomer composition. Preferably, the acid is provided in an amount ranging from about 0.1% to about 2.5% by weight, based on a total weight of the etchant/primer/adhesive monomer composition.

Initiators

Adhesive resin polymers or adhesive resin monomers for dental restoration, typically include chemical, photochemical or dual-curing free-radical initiators. See, for example, U.S. Pat. Nos.: 4,514,527; 4,521,550; 4,588,756; 4,659,751; 5,270,351; 5,498,643; 5,690,840; and 5,756,560. N-phenylglycine (NPG) is an example of an initiator which acts both as a primer, initiator and a co-initiator for promoting the polymerization of adhesive polymeric resins and adhesive monomers onto the subject dental structure undergoing restoration. CQ is an example of a photoinitiator and/or photosensitizer. Both NPG and CQ may be used in conjunction with the present invention, either singly or in combination.

Application

The etchant/primer composition in accordance with the present invention is applied to a dental structure requiring restoration for a time sufficient to etch and prime the underlying dental structure. Thereafter, optionally, the applied etchant/primer composition may be rinsed, dried or both. Then, adhesive resin(s) or adhesive monomer(s) is/are applied thereto. Typically, the adhesive resin or the adhesive monomer(s) contain an initiator. Either immediately before or immediately after application of the adhesive resin or adhesive monomer to the dental structure, curing is initiated to form a polymeric structure on the subject dental structure. Additionally, the adhesive resin or polymerized monomer is modified to the desired shape and hardness.

The etchant/primer composition may be applied as further described below. The etchant/primer is applied to the tooth surface involved in the cavity preparation (e.g., enamel and/or dentin) with an applicator brush, microtip applicator, Quick-tip™, or cotton pellet and left standing for about 60 seconds. Thereafter, any excess etchant/primer is removed, preferably with a gentle stream of air. By similar application methods (e.g., applicator brush, microtip applicator, Quick-tip™, cotton pellets or the like), the adhesive resin is applied to the relevant dental structure (e.g., to the dental structure previously coated with the etchant/primer) in a single coat or multiple coats. Then, the so-applied adhesive resin is light cured or chemically cured to polymerize the resin. Finally, an appropriate composite is placed on the partially polymerized adhesive resin and shaped with various instruments (e.g., hand instruments, rotary instruments) to the desired conformation and then polymerized by chemical polymerization or cured by light e.g. visible light.

The etchant/primer/adhesive monomer composition of the present invention is applied to a subject dental structure for a time sufficient to form the desired dental restorative structure thereon. Typically, the etchant/primer/adhesive monomer composition is provided with an initiator which may be pre-mixed therewith immediately prior to application on the dental structure or so-provided already mixed in the etchant/primer/adhesive monomer composition. Either immediately before or immediately after application of this composition to the appropriate dental structure, curing is initiated to form the desired polymeric structure. During dental restoration, the adhesive resin or polymerized monomer is modified to the desired shape and hardness.

The etchant/primer/adhesive monomer composition may be applied as further described below. The etchant/primer is applied to the tooth surface involved in the cavity preparation (e.g., enamel and/or dentin) with an applicator brush, microtip applicator, Quick-tip™, or cotton pellet and left standing for about 60 seconds. Thereafter, any excess etchant/primer is removed, preferably with a gentle stream of air. By similar application methods (e.g., applicator brush, microtip applicator, Quick-tip™, cotton pellets or the like), the adhesive resin is applied to the relevant dental structure (e.g., to the dental structure previously coated with the etchant/primer) in a single coat or multiple coats. Then, the so-applied adhesive resin is light cured or chemically cured to polymerize the resin. Finally, an appropriate composite is placed on the polymerized adhesive resin and shaped with various instruments (e.g., hand instruments, rotary instuments) to the desired conformation and then polymerized by chemical polymerization or cured by light e.g. visible light.

Kit

A kit comprising an etchant/primer composition, a polar solvent system, an adhesive monomer, and an acid may be provided as noted below. The kit comprises:

(a) at least a first container containing an etchant/primer composition, said etchant/primer composition comprising:

(i) a compound having the formula:

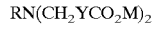

wherein $R=R^1$ or $R^2$;
$R^1$=an aromatic group;
$R^2$=a conjugated unsaturated aliphatic group;
$Y$=a single bond, $CH_2$, $CHCH_3$ or $C{=}CH_2$; and
each M is independently H, an alkali metal, an alkaline earth metal, aluminum, a transition or redox metal or an alkyl group having 1 to 18 carbon atoms, with the proviso that when both M groups are alkyl groups, said compound is capable of being easily hydrolyzed, displaced, or exchanged with other reagents present in the etchant/primer composition; and (ii) a polar solvent system; and (b) at least a second container containing an adhesive monomer system, wherein at least one of said first and second containers includes an acid.

The term "at least a first container" is intended to mean that the "etchant/primer composition" may be provided in a single "first" container or components of the "etchant/primer composition" may be split up among a plurality of "first" containers. However, it is preferable to provide the "etchant/primer composition" in a single "first" container. Likewise, the term "at least a second container" is intended to mean that the "adhesive monomer system" may be provided in a single "second" container or components of the "adhesive monomer system" may be split up among a plurality of "second" containers. Preferably, the "adhesive monomer system" is provided in a single "second" container. The term "adhesive monomer system" is intended to mean at least one adhesive monomer and at least one initiator. The contents of the "first" and "second" containers of the above-identified kit are combined either prior to application or during application thereof to the dental structure being restored.

The polar solvent system in the kit comprises solvents previously described. Such solvents include, but are not limited to, water, acetone, methyl ethyl ketone, propanol, ethanol, dimethylformamide, dimethylacetamide, dimethylsulfoxide, 1-methyl-2-pyrrolidinone or combinations and mixtures thereof.

Preferably, the acid in the kit is nitric acid. The nitric acid in the kit is provided to yield an amount of the acid, preferably, from about 0.05% to about 5.0% by weight, and more preferably, from about 0.1% to about 2.5% by weight, based on a total weight of the contents of the first and second containers.

The following examples are provided to illustrate various embodiments of the present invention. These examples are not intended to limit the scope of the appended claims.

EXAMPLES

Unless indicated otherwise, all percentages are percentages by weight based on a total weight of the composition being applied. Application of the various components and light curing was accomplished through an iris having the diameter indicated in the Tables below. Iris diameter was measured in millimeter (mm) units. The load is measured in kilo newtons (kN). The shear bond strength was measured in MPa units. The composite resin used was a hybrid composite, typically TPH™ (L.D. Caulk, Millford, Del.; urethane modified Bis-GMA (urethane modified bisphenol gycidyl methacrylate), TEGDMA (triethylene glycol dimethacrylate), and barium silicate glass filler (avg. particle size of about 0.7 μm)). SBS measurements were taken after the fully treated dental specimen was stored for 24 hours in $H_2O$ at 23° C.

Comparative Example 1

The procedure noted below was followed to obtain the shear bond strength (SBS) values noted in Tables 1–4. The results in Tables 1–4 reflect the use of an iminodiacetic acid without the addition of an acidic component being added thereto. The specific primers utilized were:

1. 6.3% by weight PIDAA in $H_2O$/acetone (1:1 v/v), and
2. 12.5% by weight PIDAA in $H_2O$/acetone (1:1 v/v).

A bovine enamel surface was treated with either primer 1. or 2. for 60 seconds. Any excess primer was then gently removed with air. Thereafter, the following adhesive polymer or adhesive monomer was applied by the protocol noted below:

a) 15.1% PMGDM in acetone with 0.07% camphorquinone (CQ) was light cured for 20 seconds and then applied to the above-treated bovine enamel surface through an iris having an iris diameter as indicated in the Tables below and then light cured for 20 seconds followed by the application of 60% bis-GMA and 40% HEMA. The so-treated surface was then light cured for another 60 seconds.

b) Alternatively, the above-noted PMGDM in acetone with CQ of protocol a) was not applied. Instead, the 60% bis-GMA and 40% HEMA were applied through the iris and light cured for 60 seconds.

TABLE 1

| Assembly # | Protocol | Iris Diam (mm) | Load (kN) | SBS (MPa) | Mean (MPa) | SD (MPa) |
|---|---|---|---|---|---|---|
| 214 | 1a | 3.98 | 0.182 | 14.6 | | |
| 153 | 1a | 3.98 | 0.107 | 8.6 | | |
| A4 | 1a | 3.98 | 0.195 | 15.7 | | |
| 405 | 1a | 3.98 | 0.160 | 12.8 | | |
| 95 | 1a | 3.98 | 0.178 | 14.3 | 13.2 | 2.8 |

TABLE 2

| Assembly # | Protocol | Iris Diam (mm) | Load (kN) | SBS (MPa) | Mean (MPa) | SD (MPa) |
|---|---|---|---|---|---|---|
| 213 | 1b | 3.98 | 0.016 | 1.3 | | |
| 38 | 1b | 3.97 | 0.095 | 7.7 | | |
| A9 | 1b | 3.97 | 0.176 | 14.2 | | |
| 206 | 1b | 3.97 | 0.050 | 4.0 | | |
| 69 | 1b | 3.97 | 0.068 | 5.5 | | |
| A28 | 1b | 3.97 | 0.082 | 6.6 | 6.5 | 4.4 |

TABLE 3

| Assembly # | Protocol | Iris Diam (mm) | Load (kN) | SBS (MPa) | Mean (MPa) | SD (MPa) |
|---|---|---|---|---|---|---|
| 38A | 2a | 3.97 | 0.157 | 12.7 | | |
| 7AL | 2a | 3.94 | 0.213 | 17.5 | | |
| 89 | 2a | 3.94 | 0.171 | 14.0 | | |
| 36 | 2a | 3.94 | 0.189 | 15.5 | | |
| 212 | 2a | 3.94 | 0.188 | 15.4 | 15.0 | 1.8 |

TABLE 4

| Assembly # | Protocol | Iris Diam (mm) | Load (kN) | SBS (MPa) | Mean (MPa) | SD (MPa) |
|---|---|---|---|---|---|---|
| 00 | 2b | 3.93 | 0.429 | 35.4 | | |
| A20 | 2b | 3.93 | 0.468 | 38.6 | | |
| 4 | 2b | 3.93 | 0.285 | 23.5 | | |
| 26 | 2b | 3.93 | 0.398 | 32.9 | | |
| 415 | 2b | 3.93 | 0.031 | 2.5 | 26.6 | 14.6 |

Comparative Example 2

The same procedure outlined in Example 1 was used to yield the results indicated in Table 5 below, except that the 6.3% PIDAA and the 12.5% PIDAA solutions of primers 1. and 2. were replaced with $H_3PO_4$ and protocol b) was utilized.

TABLE 5

| Assembly # | Protocol | Iris Diam (mm) | Load (kN) | SBS (MPa) | Mean (MPa) | SD (MPa) |
|---|---|---|---|---|---|---|
| 101 | $H_3PO_4$ b | 3.91 | 0.040 | 3.3 | | |
| 117 | $H_3PO_4$ b | 3.91 | 0.020 | 1.7 | | |
| A11 | $H_3PO_4$ b | 3.91 | 0.056 | 4.6 | | |
| 126 | $H_3PO_4$ b | 3.92 | 0.077 | 6.4 | 4.0 | 2.0 |

Example 3

The following procedure was used to treat bovine enamel:

1A) 1.25% $HNO_3$ and 6.4% PIDAA in acetone/$H_2O$ was applied to bovine enamel for 60 seconds. Any excess of $HNO_3$ and PIDAA was then removed with air. Thereafter, five coats of a mixture of 20% PMGDM and 0.07% CQ in acetone were applied over the mixture of $HNO_3$ and PIDAA and then light cured for 20 seconds. Then, a mixture of 60% bis-GMA and 40% HEMA was applied and light cured for 20 seconds. Next, a composite resin of TPH™ (L.D. Caulk, Millford, Del.; urethane-modified Bis-GMA, TEGDMA, and barium silicate glass filler (avg. particle size of about 0.7 μm)) was applied and light cured for 60 seconds. The SBS results so-obtained are provided in Table 6 below.

TABLE 6

| Assembly # | Protocol | Iris Diam (mm) | Load (kN) | SBS (MPa) | Mean (MPa) | SD (MPa) |
|---|---|---|---|---|---|---|
| 131 | 1A | 3.97 | 0.280 | 22.7 | | |
| 47 | 1A | 3.98 | 0.342 | 27.5 | | |
| 36 | 1A | 3.95 | 0.279 | 22.8 | | |
| 112 | 1A | 3.94 | 0.226 | 18.5 | | |
| 36 | 1A | 3.95 | 0.137 | 11.2 | | |
| 39 | 1A | 3.95 | 0.456 | 37.2 | | |
| 108 | 1A | 3.95 | 0.428 | 34.9 | | |
| 72 | 1A | 3.95 | 0.538 | 43.9 | | |

TABLE 6-continued

| Assembly # | Protocol | Iris Diam (mm) | Load (kN) | SBS (MPa) | Mean (MPa) | SD (MPa) |
|---|---|---|---|---|---|---|
| 47 | 1A | 3.97 | 0.353 | 28.5 | | |
| 131 | 1A | 3.97 | 0.390 | 31.5 | 27.9 | 9.6 |

1B) The same procedures as outlined above in connection with Table 6 above were utilized, except that the 1.25% $HNO_3$ and 6.4% PIDAA in acetone/$H_2O$ solution was applied for 30 seconds instead of 60 seconds. The results of such application on shear bond strength are provided in Table 7 below.

TABLE 7

| Assembly # | Protocol | Iris Diam (mm) | Load (kN) | SBS (MPa) | Mean (MPa) | SD (MPa) |
|---|---|---|---|---|---|---|
| 138 | 1B | 3.97 | 0.549 | 44.4 | | |
| 105 | 1B | 3.97 | 0.239 | 19.3 | | |
| A-13 | 1B | 3.97 | 0.296 | 23.9 | | |
| 97 | 1B | 3.98 | 0.403 | 32.4 | | |
| 50 | 1B | 3.95 | 0.425 | 34.7 | | |
| 425 | 1B | 3.95 | 0.238 | 19.4 | | |
| A26 | 1B | 3.95 | 0.208 | 17.0 | | |
| 105 | 1B | 3.95 | 0.328 | 26.8 | | |
| F3 | 1B | 3.97 | 0.294 | 23.8 | | |
| 138 | 1B | 3.97 | 0.387 | 31.3 | 27.3 | 8.5 |

The same procedures outlined as 1A) were utilized to obtain the results indicated in Table 8 below, except that instead of the solution of 1.25% $HNO_3$ and 6.4% PIDAA in acetone/$H_2O$, a solution of 2.5% $HNO_3$ and 6.4% PIDAA in acetone/$H_2O$ was applied. Further, any excess $HNO_3$ and PIDAA was not removed with air.

TABLE 8

| Assembly # | Protocol | Iris Diam (mm) | Load (kN) | SBS (MPa) | Mean (MPa) | SD (MPa) |
|---|---|---|---|---|---|---|
| A-3 | 3A | 3.97 | 0.271 | 21.9 | | |
| 81 | 3A | 3.97 | 0.415 | 33.5 | | |
| 96 | 3A | 3.98 | 0.483 | 38.8 | | |
| 5 | 3A | 3.95 | 0.387 | 31.6 | | |
| A2 | 3A | 3.95 | 0.481 | 39.3 | | |
| 81 | 3A | 3.95 | 0.316 | 25.8 | | |
| A13 | 3A | 3.95 | 0.417 | 34.0 | | |
| A10 | 3A | 3.95 | 0.509 | 41.6 | | |
| 97 | 3A | 3.95 | 0.399 | 32.5 | | |
| 306 | 3A | 3.97 | 0.362 | 29.2 | 32.8 | 6.1 |

The same procedures outlined for obtaining the results in Table 8 were used for obtaining the results indicated in Table 9 below, except that the 2.5% $HNO_3$ and 6.4% PIDAA in acetone/$H_2O$ solution was applied for 30 seconds instead of 60 seconds.

TABLE 9

| Assembly # | Protocol | Iris Diam (mm) | Load (kN) | SBS (MPa) | Mean (MPa) | SD (MPa) |
|---|---|---|---|---|---|---|
| 108 | 3B | 3.97 | 0.273 | 22.0 | | |
| 149 | 3B | 3.98 | 0.416 | 33.4 | | |
| 306 | 3B | 3.98 | 0.299 | 24.0 | | |
| 39 | 3B | 3.95 | 0.309 | 25.2 | | |
| 5 | 3B | 3.95 | 0.361 | 29.5 | | |
| 96 | 3B | 3.95 | 0.321 | 26.2 | | |
| A104 | 3B | 3.95 | 0.347 | 28.3 | | |

TABLE 9-continued

| Assembly # | Protocol | Iris Diam (mm) | Load (kN) | SBS (MPa) | Mean (MPa) | SD (MPa) |
|---|---|---|---|---|---|---|
| A3 | 3B | 3.97 | 0.221 | 17.8 | | |
| 112 | 3B | 3.97 | 0.413 | 33.4 | | |
| 149 | 3B | 3.97 | 0.502 | 40.6 | 28.0 | 6.5 |

Example 4

Bovine enamel was treated as follows: a mixture 2.5% $HNO_3$ and 6.3% PIDAA in acetone/$H_2O$ was applied for 30 seconds. Then, five coats of a mixture of 20% PMGDM and 0.07% CQ in acetone were applied and light cured for 20 seconds. Thereafter, a mixture of 60% bis-GMA and 40% HEMA was applied and light cured for 20 seconds. Finally, a composite resin of TPH™ (L.D. Caulk, Millford, Del.; urethane-modified Bis-GMA, TEGDMA, and barium silicate glass filler (avg. particle size of about 0.71 $\mu$m)) was applied and light cured for 60 seconds. The SBS results so-obtained are indicated in Table 10 below.

TABLE 10

| Assembly # | Protocol | Iris Diam (mm) | Load (kN) | SBS (MPa) | Mean (MPa) | SD (MPa) |
|---|---|---|---|---|---|---|
| A10 | 1 | 3.97 | 0.237 | 19.1 | | |
| A3 | 1 | 3.97 | 0.245 | 19.8 | | |
| 73 | 1 | 3.97 | 0.158 | 12.8 | | |
| F3 | 1 | 3.97 | 0.097 | 17.8 | | |
| 149 | 1 | 3.97 | 0.195 | 15.8 | | |
| 5 | 1 | 3.95 | 0.383 | 32.2 | | |
| 81 | 1 | 3.95 | 0.304 | 24.8 | | |
| A2 | 1 | 3.95 | 0.211 | 17.2 | 18.7 | 7.4 |

Example 5

The following procedure was used to obtain the SBS results indicated in Table 11 below. To bovine enamel, a 2.5% aqueous $HNO_3$ solution was applied for 30 seconds. Thereafter, a 6.3% PIDAA in acetone/water solution was applied. Then, five coats of a mixture of 20% PMGDM and 0.07% CQ in acetone was applied and light cured for 20 seconds. Next, a mixture of 60% bis-GMA and 40% HEMA was applied and light cured for 20 seconds. Finally, a composite resin of TPH™ (L.D. Caulk, Millford, Del.; urethane-modified Bis-GMA, TEGDMA, and barium silicate glass filler (avg. particle size of about 0.7 $\mu$m)) was applied and light cured for 60 seconds.

TABLE 11

| Assembly # | Protocol | Iris Diam (mm) | Load (kN) | SBS (MPa) | Mean (MPa) | SD (MPa) |
|---|---|---|---|---|---|---|
| 39 | 2 | 3.97 | 0.367 | 29.6 | | |
| 131 | 2 | 3.95 | 0.228 | 18.6 | | |
| 72 | 2 | 3.95 | 0.146 | 11.9 | | |
| 425 | 2 | 3.95 | 0.245 | 20.0 | | |
| 36 | 2 | 3.95 | 0.389 | 31.7 | | |
| 47 | 2 | 3.95 | 0.245 | 20.0 | | |
| 306 | 2 | 3.95 | 0.201 | 16.4 | | |
| A13 | 2 | 3.95 | 0.366 | 29.9 | 22.3 | 7.2 |

Comparative Example 6

The following procedure was utilized to obtain the SBS results indicated in Table 12 below. Bovine enamel was treated with a 10% aqueous solution of $H_3PO_4$ for 30 seconds. Then, a mixture of 60% bis-GMA and 40% HEMA was applied and light cured for 20 seconds. Finally, a composite resin of TPH™ (L.D. Caulk, Millford, Del.; urethane-modified Bis-GMA, TEGDMA, and barium silicate glass filler (avg. particle size of about 0.7 μm)) was applied and light cured for 60 seconds.

TABLE 12

| Assembly # | Protocol | Iris Diam (mm) | Load (kN) | SBS (MPa) | Mean (MPa) | SD (MPa) |
|---|---|---|---|---|---|---|
| A26 | 3 | 3.99 | 0.251 | 20.1 | | |
| 138 | 3 | 3.97 | 0.380 | 30.7 | | |
| 112 | 3 | 3.97 | 0.384 | 31.0 | | |
| 97 | 3 | 3.87 | 0.397 | 32.1 | | |
| 108 | 3 | 3.95 | 0.400 | 32.6 | | |
| 105 | 3 | 3.95 | 0.223 | 18.2 | | |
| 96 | 3 | 3.95 | 0.409 | 33.3 | | |
| 50 | 3 | 3.95 | 0.298 | 24.3 | 27.8 | 6.0 |

Example 7

The following procedures were utilized to obtain results indicated in Tables 13 and 13a below. To dentin, 20 mL of 0.3M PIDAA in acetone:$H_2O$ (1:1 v/v) was applied for 60 seconds. Then, the PIDAA solution was either rinsed and dried (indicated as "RD") or just air dried (indicated as "D"). Thereafter, five coats of 20% PMGDM and 0.07% CQ in acetone were applied to the treated dentin surface, the solvent evaporated with air and light cured for 20 seconds. Next, a composite resin of TPH™ (L.D. Caulk, Millford, Del.; urethane-modified Bis-GMA, TEGDMA, and barium silicate glass filler (avg. particle size of about 0.7 μm)) and light cured for 60 seconds.

TABLE 13

| Assembly # | Protocol | Iris Diam (mm) | Load (kN) | SBS (MPa) | Mean (MPa) | SD (MPa) |
|---|---|---|---|---|---|---|
| R5 | 1a RD | 3.96 | 0.399 | 32.4 | | |
| M49 | 1a RD | 3.96 | 0.254 | 20.6 | | |
| M70 | 1a RD | 3.96 | 0.489 | 39.7 | | |
| 163 | 1a RD | 3.97 | 0.284 | 23.0 | | |
| M60 | 1a RD | 3.97 | 0.272 | 22.0 | 27.5 | 8.2 |
| M67 | 1a D | 3.96 | 0.269 | 21.9 | | |
| 52 | 1a D | 3.96 | 0.490 | 39.8 | | |
| 6 | 1a D | 3.96 | 0.307 | 24.9 | | |
| 116 | 1a D | 3.96 | 0.362 | 29.4 | | |
| 2AL | 1a D | 3.96 | 0.430 | 34.9 | 30.2 | 7.3 |

TABLE 13a

| Assembly # | Protocol | Iris Diam (mm) | Load (kN) | SBS (MPa) | Mean (MPa) | SD (MPa) |
|---|---|---|---|---|---|---|
| S49 | 1a RD | 3.97 | 0.361 | 29.2 | | |
| 44 | 1a RD | 3.97 | 0.107 | 8.7 | | |
| R5 | 1a RD | 3.96 | 0.248 | 20.2 | | |
| 2AL | 1a RD | 3.96 | 0.277 | 22.5 | | |
| 114 | 1a RD | 3.98 | 0.363 | 29.2 | 21.9 | 8.4 |
| S43 | 1a D | 3.97 | 0.327 | 26.4 | | |
| 96 | 1a D | 3.97 | 0.333 | 26.9 | | |
| R28 | 1a D | 3.95 | 0.318 | 26.0 | | |
| 402 | 1a D | 3.95 | 0.209 | 17.1 | | |
| 158 | 1a D | 3.98 | 0.325 | 26.1 | 24.5 | 4.2 |

The same procedures as outlined above in this Example were used, except that instead of a 60 second application of the 0.3M PIDAA solution, a 30 second was made. The so-obtained SBS results are provided in Tables 14 and 14a below.

TABLE 14

| Assembly # | Protocol | Iris Diam (mm) | Load (kN) | SBS (MPa) | Mean (MPa) | SD (MPa) |
|---|---|---|---|---|---|---|
| 203 | 1b RD | 3.96 | 0.212 | 17.2 | | |
| 152 | 1b RD | 3.96 | 0.344 | 27.9 | | |
| 93 | 1b RD | 3.97 | 0.246 | 19.9 | | |
| 158 | 1b RD | 3.97 | 0.222 | 17.9 | | |
| S27 | 1b RD | 3.97 | 0.190 | 15.4 | 19.7 | 4.9 |
| G19 | 1b D | 3.96 | 0.578 | 46.9 | | |
| 401 | 1b D | 3.96 | 0.213 | 17.3 | | |
| 96 | 1b D | 3.97 | 0.390 | 31.5 | | |
| 402 | 1b D | 3.96 | 0.377 | 30.6 | | |
| S49 | 1b D | 3.97 | 0.265 | 21.4 | 29.5 | 11.4 |

TABLE 14a

| Assembly # | Protocol | Iris Diam (mm) | Load (kN) | SBS (MPa) | Mean (MPa) | SD (MPa) |
|---|---|---|---|---|---|---|
| 163 | 1b RD | 3.97 | 0.338 | 27.3 | | |
| 76 | 1b RD | 3.96 | 0.368 | 29.9 | | |
| 1 | 1b RD | 3.96 | 0.375 | 30.5 | | |
| M82 | 1b RD | 3.96 | 0.320 | 26.0 | | |
| 101 | 1b RD | 3.95 | 0.420 | 34.3 | 29.6 | 3.2 |
| 157 | 1b D | 3.97 | 0.473 | 38.2 | | |
| 105 | 1b D | 3.96 | 0.415 | 33.7 | | |
| M35 | 1b D | 3.96 | 0.231 | 18.8 | | |
| 555 | 1b D | 3.98 | 0.321 | 25.8 | | |
| 412 | 1b D | 3.98 | 0.490 | 39.4 | 31.2 | 8.7 |

Example 8

The same procedures outlined in Example 6 were utilized, except that instead of 0.3M PIDAA in acetone:$H_2O$ (1:1 v/v), a solution of 0.3M PIDAA in acetone:$H_2O$ (1:1 v/v) and 2.5% $HNO_3$ (aqueous) was applied for 60 seconds followed by rinsing and drying (RD) or just air drying (D). The so-obtained SBS results are indicated in Tables 15 and 15a below.

TABLE 15

| Assembly # | Protocol | Iris Diam (mm) | Load (kN) | SBS (MPa) | Mean (MPa) | SD (MPa) |
|---|---|---|---|---|---|---|
| 122 | 1c RD | 3.96 | 0.344 | 28.0 | | |
| 555 | 1c RD | 3.96 | 0.578 | 47.0 | | |
| M132 | 1c RD | 3.97 | 0.349 | 28.2 | | |
| 144 | 1c RD | 3.97 | 0.289 | 23.3 | | |
| M87 | 1c RD | 3.97 | 0.341 | 27.6 | 30.8 | 9.25 |
| 412 | 1c D | 3.96 | 0.432 | 35.1 | | |
| M82 | 1c D | 3.96 | 0.219 | 17.8 | | |
| 1 | 1c D | 3.96 | 0.349 | 28.3 | | |
| M40 | 1c D | 3.97 | 0.246 | 19.9 | | |
| 164 | 1c D | 3.97 | 0.363 | 29.3 | 26.1 | 7.13 |

TABLE 15a

| Assembly # | Protocol | Iris Diam (mm) | Load (kN) | SBS (MPa) | Mean (MPa) | SD (MPa) |
|---|---|---|---|---|---|---|
| 93 | 1c RD | 3.97 | 0.350 | 28.2 | | |
| 203 | 1c RD | 3.96 | 0.265 | 21.5 | | |
| 52 | 1c RD | 3.96 | 0.334 | 27.2 | | |
| 164 | 1c RD | 3.95 | 0.302 | 24.7 | | |
| 401 | 1c RD | 3.98 | 0.312 | 25.1 | 25.3 | 2.6 |
| 144 | 1c D | 3.97 | 0.352 | 28.5 | | |

TABLE 15a-continued

| Assembly # | Protocol | Iris Diam (mm) | Load (kN) | SBS (MPa) | Mean (MPa) | SD (MPa) |
|---|---|---|---|---|---|---|
| M40 | 1c D | 3.97 | 0.344 | 27.8 | | |
| M60 | 1c D | 3.96 | 0.350 | 28.4 | | |
| 108 | 1c D | 3.95 | 0.291 | 23.7 | | |
| 122 | 1c D | 3.98 | 0.182 | 14.6 | 24.6 | 5.9 |

Example 9

The same procedures outlined in Example 7 were utilized, except that the solution of 0.3M PIDAA in acetone:H$_2$O (1:1 v/v) and 2.5% HNO$_3$ was applied for 30 seconds instead of 60 seconds. Then, the so-treated specimen was rinsed and dried (RD) or just air dried (D) to obtain the results indicated in Tables 16 and 16a below.

TABLE 16

| Assembly # | Protocol | Iris Diam (mm) | Load (kN) | SBS (MPa) | Mean (MPa) | SD (MPa) |
|---|---|---|---|---|---|---|
| 101 | 1d RD | 3.96 | 0.633 | 51.4 | | |
| M65 | 1d RD | 3.96 | 0.392 | 31.9 | | |
| M18 | 1d RD | 3.96 | 0.100 | 8.1 | | |
| 105 | 1d RD | 3.96 | 0.344 | 27.9 | | |
| 44 | 1d RD | 3.97 | 0.369 | 29.8 | 29.8 | 15.4 |
| 120 | 1d D | 3.96 | 0.347 | 28.1 | | |
| S43 | 1d D | 3.96 | 0.352 | 28.6 | | |
| 157 | 1d D | 3.97 | 0.309 | 24.9 | | |
| R29 | 1d D | 3.97 | 0.305 | 24.6 | | |
| 313 | 1d D | 3.97 | 0.272 | 22.0 | 25.7 | 2.74 |

TABLE 16a

| Assembly # | Protocol | Iris Diam (mm) | Load (kN) | SBS (MPa) | Mean (MPa) | SD (MPa) |
|---|---|---|---|---|---|---|
| 152 | 1d RD | 3.97 | 0.225 | 18.2 | | |
| 148 | 1d RD | 3.97 | 0.278 | 22.4 | | |
| M132 | 1d RD | 3.97 | 0.340 | 27.4 | | |
| M49 | 1d RD | 3.98 | 0.306 | 24.6 | | |
| 96 | 1d RD | 3.98 | 0.393 | 31.6 | 24.8 | 5.1 |
| S27 | 1d D | 3.97 | 0.136 | 11.0 | | |
| M70 | 1d D | 3.97 | 0.453 | 36.6 | | |
| 313 | 1d D | 3.97 | 0.374 | 30.2 | | |
| M87 | 1d D | 3.96 | 0.365 | 29.6 | | |
| 116 | 1d D | 3.96 | 0.373 | 30.3 | 27.5 | 9.7 |

All patents, publications and other references cited in this application are incorporated herein by reference in their entirety.

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. An etchant/primer composition comprising:
   a compound having the formula:

RN(CH$_2$YCO$_2$M)$_2$ wherein R=R$^1$ or R$^2$;
   R$^1$=an aromatic group;
   R$^2$=a conjugated unsaturated aliphatic group;
   Y=a single bond, CH$_2$, CHCH$_3$ or C=CH$_2$; and
   each M is independently H, an alkali metal, an alkaline earth metal, aluminum, a transition or redox metal or an alkyl group having 1 to 18 carbon atoms, with the proviso that when both M groups are alkyl groups, said compound corresponding to said formula is hydrolyzed, displaced, or exchanged with other reagents present in the etchant/primer composition;
   a polar solvent system; and
   nitric acid.

2. The etchant/primer composition of claim 1, wherein said nitric acid is present in an amount ranging from about 0.05% to about 5.0% by weight based on a total weight of said etchant/primer composition.

3. The etchant/primer composition of claim 2, wherein said nitric acid is present in an amount ranging from about 0.1% to about 2.5% by weight based on said total weight.

4. The etchant/primer composition of claim 1, wherein said polar solvent system comprises an aqueous solvent.

5. The etchant/primer composition of claim 1, wherein said polar solvent system comprises acetone and water.

6. The etchant/primer composition of claim 1, wherein said polar solvent system comprises a solvent selected from the group consisting of water, acetone, dimethylsulfoxide, ethanol and mixtures thereof.

7. The etchant/primer composition of claim 1,
   wherein R=R$^1$ and R$^1$ comprises C$_6$H$_5$ or C$_6$H$_4$R$^3$;
   wherein R$^3$=N(CH$_2$CO$_2$M)$_2$; C$_6$H$_4$N(CH$_2$CO$_2$M)$_2$; R$^5$O (CH$_2$)$_2$OC$_6$H$_4$N(CH$_2$CO$_2$M)$_2$; CH=CH$_2$; CO$_2$H; F; Cl; Br; I; OH; SH; (m- or p-) CH$_2$C$_6$H$_4$(m- or p-) CH=CH$_2$; OCOC (R$^4$)=CH$_2$; NR$^4$COC(R$^4$)=CH$_2$; (CH$_2$)$_2$OCOC(R$^4$)=CH$_2$; C$_6$H$_5$; an alkyl group having 1 to 12 carbon atoms; HOCH$_2$; HOCH$_2$CH$_2$; R$^5$$_2$N; R$^6$O; R$^6$S; R$^6$CO; R$^7$CONH; R$^7$COCO,
   wherein R$^4$=H or CH$_3$;
   wherein R$^5$=H or an alkyl group having 1 to 8 carbon atoms;
   wherein R$^6$=an alkyl group having from 1 to 6 carbon atoms; and
   wherein R$^7$=an alkyl group having 1 to 6 carbon atoms.

8. The etchant/primer composition of claim 1, wherein said alkyl M group is t-butyl.

9. An etchant/primer composition consisting of:
   a compound having the formula:

RN(CH$_2$YCO$_2$M)$_2$ wherein R=R$^1$ or R$^2$;
   R$^1$=an aromatic group;
   R$^2$=a conjugated unsaturated aliphatic group;
   Y=a single bond, CH$_2$, CHCH$_3$ or C=CH$_2$; and
   each M is independently H, an alkali metal, an alkaline earth metal, aluminum, a transition or redox metal or an alkyl group having 1 to 18 carbon atoms, with the proviso that when both M groups are alkyl groups, said compound corresponding to said formula is hydrolyzed, displaced, or exchanged with other reagents present in the etchant/primer composition;
   a polar solvent system; and
   nitric acid.

10. The etchant/primer composition of claim 9, wherein said nitric acid is present in an amount ranging from about 0.05% to about 5.0% by weight based on a total weight of said etchant/primer composition.

11. The etchant/primer composition of claim 10, wherein said nitric acid is present in an amount ranging from about 0.1% to about 2.5% by weight based on said total weight.

12. The etchant/primer composition of claim 9, wherein said polar solvent system comprises an aqueous solvent.

13. The etchant/primer composition of claim 9, wherein said polar solvent system comprises acetone and water.

14. The etchant/primer composition of claim 13, wherein a ratio of said water to said acetone is in the range from about 5:90 to about 90:5 by volume.

15. The etchant/primer composition of claim 9, wherein said polar solvent system comprises a solvent selected from the group consisting of water, acetone, dimethylsulfoxide, ethanol and mixtures thereof.

16. The etchant/primer composition of claim 9, wherein $R=R^1$ and $R^1$ comprises $C_6H_5$ or $C_6H_4R^3$;

wherein $R^3=N(CH_2CO_2M)_2$; $C_6H_4N(CH_2CO_2M)_2$; $R^5O(CH_2)_2OC_6H_4N(CH_2CO_2M)_2$; $CH=CH_2$; $CO_2H$; F; Cl; Br; I; OH; SH; (m- or p-) $CH_2C_6H_4$(m- or p-) $CH=CH_2$; $OCOC(R^4)=CH_2$; $NR^4COC(R^4)=CH_2$; $(CH_2)_2OCOC(R^4)=CH_2$; $C_6H_5$; an alkyl group having 1 to 12 carbon atoms; $HOCH_2HOCH_2CH_2$; $R^5_2N$; $R^6O$; $R^6S$; $R^6CO$; $R^7CONH$; $R^7COCO$, wherein $R^4=H$ or $CH_3$;

wherein $R^5=H$ or an alkyl group having 1 to 8 carbon atoms;

wherein $R^6=$an alkyl group having from 1 to 6 carbon atoms; and wherein $R^7=$an alkyl group having 1 to 6 carbon atoms.

17. The etchant/primer composition of claim 9, wherein said alkyl M group is t-butyl.

18. An etchant/primer composition comprising:

a compound having the formula:

$$RN(CH_2YCO_2M)_2$$

wherein $R=R^1$ or $R^2$;

$R^1=$an aromatic group;

$R^2=$a conjugated unsaturated aliphatic group;

$Y=$a single bond, $CH_2$, $CHCH_3$ or $C=CH_2$; and each M is independently H, an alkali metal, an alkaline earth metal, aluminum, a transition or redox metal or an alkyl group having 1 to 18 carbon atoms;

a polar solvent system; and nitric acid.

19. The etchant/primer composition of claim 18, wherein said nitric acid is present in an amount ranging from about 0.05% to about 5.0% by weight based on a total weight of said etchant/primer composition.

20. The etchant/primer composition of claim 19, wherein said nitric acid is present in an amount ranging from about 0.1% to about 2.5% by weight based on said total weight.

21. The etchant/primer composition of claim 18, wherein said polar solvent system comprises an aqueous solvent.

22. The etchant/primer composition of claim 18, wherein said polar solvent system comprises acetone and water.

23. The etchant/primer composition of claim 22, wherein a ratio of said water to said acetone is in the range from about 5:90 to about 90:5 by volume.

24. The etchant/primer composition of claim 18, wherein said polar solvent system comprises a solvent selected from the group consisting of water, acetone, dimethylsulfoxide, ethanol and mixtures thereof.

25. The etchant/primer composition of claim 18, wherein $R=R^1$ and $R^1$ comprises $C_6H_5$ or $C_6H_4R^3$;

wherein $R^3=N(CH_2CO_2M)_2$; $C_6H_4N(CH_2CO_2M)_2$; $R^5O(CH_2)_2OC_6H_4N(CH_2CO_2M)_2$; $CH=CH_2$; $CO_2H$; F; Cl; Br; I; OH; (m- or p-) $CH_2C_6H_4$(m- or p-) $CH=CH_2$; $OCOC(R^4)=CH_2$; $NR^4COC(R^4)=CH_2$; $(CH_2)_2OCOC(R^4)=CH_2$; $C_6H_5$ ; an alkyl group having 1 to 12 carbon atoms; $HOCH_2$; $HOCH_2CH_2$; $R^5_2N$; $R^6O$; $R^6S$; $R^6CO$; $R^7CONH$; $R^7COCO$, wherein $R^4=H$ or $CH_3$;

wherein $R^5=H$ or an alkyl group having 1 to 8 carbon atoms;

wherein $R^6=$an alkyl group having from 1 to 6 carbon atoms; and wherein $R^7=$an alkyl group having 1 to 6 carbon atoms.

26. The etchant/primer composition of claim 18, wherein said alkyl M group is t-butyl.

* * * * *